(12) United States Patent
Wu et al.

(10) Patent No.: US 7,608,455 B2
(45) Date of Patent: Oct. 27, 2009

(54) MODIFIED RECONSTITUTED BASEMENT MEMBRANE COMPOSITION FOR ASSAY SYSTEM

(75) Inventors: Min Wu, Carlisle, MA (US); Frank J. Mannuzza, Chelmsford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/010,679

(22) Filed: Dec. 13, 2004

(65) Prior Publication Data

US 2005/0175705 A1    Aug. 11, 2005

Related U.S. Application Data

(63) Continuation-in-part of application No. 10/909,636, filed on Aug. 2, 2004, now abandoned.

(60) Provisional application No. 60/496,413, filed on Aug. 20, 2003.

(51) Int. Cl.
*C12N 5/00*     (2006.01)

(52) U.S. Cl. .................. 435/402; 435/395; 435/397

(58) Field of Classification Search .............. None
See application file for complete search history.

(56) References Cited

U.S. PATENT DOCUMENTS 4,829,000 A * 5/1989 Kleinman et al. ........... 435/408
5,260,210 A * 11/1993 Rubin et al. ................. 435/325
5,405,772 A * 4/1995 Ponting ...................... 435/378
5,629,287 A * 5/1997 Brown et al. .................. 514/8
5,643,787 A   7/1997 Barsky et al.
5,731,417 A * 3/1998 Swiderek et al. ............ 530/356

OTHER PUBLICATIONS

Schneider et al, Clinical Materials, 1993, vol. 13, pp. 51-55.*
Kleinman et al, Analytical Biochemistry, 1987, vol. 166, pp. 1-13.*
Schneider et al, Thrombosis and Haemostasis, 1997, vol. 78, pp. 1392-1398.*
DiMilla et al, Journal of Cell Biology, 1993, vol. 122, No. 3, pp. 729-737.*
Kedeshian et al, Cancer Letters, 1998, vol. 123, pp. 215-226.*
Invitrogen's "DMEM Dulbecco's Modified Eagle Medium" Product Description (3 Pages), retrieved from Invitrogen website on Jun. 29, 2006    http://www.invitrogen.com/content/sfs/ProductNotes/ DMEM%20-RD-MKT-HL050602.pdf?ProductNoteID=22.*
Invitrogen's "Technical Resources- Media Formulations: DMEM" (1 Page), retrieved from Invitrogen website on Jun. 29, 2006 http://www.invitrogen.com/content.cfm?pageID=95&fusaction=MediaForm.dsp_mediaForm&productID=50.*

(Continued)

*Primary Examiner*—Allison M Ford
(74) *Attorney, Agent, or Firm*—Hoffman & Baron LLP

(57) ABSTRACT

A modified reconstituted extracellular matrix composition is provided herein. The composition includes an extracellular matrix and at least one exogenous component selected from heparin, fibronectin and laminin. The composition may have a basic pH. Additionally, provided herein is a cell culturing system including a substrate and a coating thereon of the composition to assess potential stimulators and/or inhibitors for their effects on various cell cultures while increasing the signal dynamic range.

22 Claims, 5 Drawing Sheets

OTHER PUBLICATIONS

"Fibronectin from bovine plasma" Product Information Sheet, Sigma-Aldrich; retrieved from Online Product Catalog (URL: <http://www.sigmalaldrich.com/catalog/search/ProductDetail/SIGMA/F1141> on May 10, 2007 (2 pages).*

Kleinman et al, "Basement Membrane Complexes with Biological Activity" Biochemistry, 1986, vol. 25, pp. 312-318.*

"Heparin Unit" The Online Medical Dictionary (2000). Retrieved Sep. 19, 2008 from URL:<http://cancerweb.ncl.ac.uk/cgi-bin/omd?Howell+unit>.*

Kubota, Role of Laminin and Basement Membrane in the Morphological Differentiation of Human Endothelial Cells into Capillary-like Structures, The Journal of Cell Biology, Oct. 1988, pp. 1589-1598, vol. 107.

Nicosia, Fibronectin Promotes the Elongation of Microvessels During Angiogenesis In Vitro, Journal of Cellular Physiology, 1993, pp. 654-661, vol. 154.

Passaniti, A Simple, Quantitative Method for Assessing Angiogenesis and Antiagiogenic Agents Using Reconstituted Basement Membrane, Heparain, and Fibroblast Growth Factor, Laborabory Investigation, 1992, pp. 519-528, vol. 67, No. 4.

BD Biosciences, Product Specification Sheet—BD Matrigel TM Basement Membrane Mix, Online, Feb. 15. 2002, pp. 1-3.

Merrill, Poly(ethylene oxide) star molecules: Synthesis, characterizations and applications in medicine and biology, J. Biomater. Sci. Polymer. Edn., 1993, pp. 1-11, vol. 5, No. 1/2.

* cited by examiner

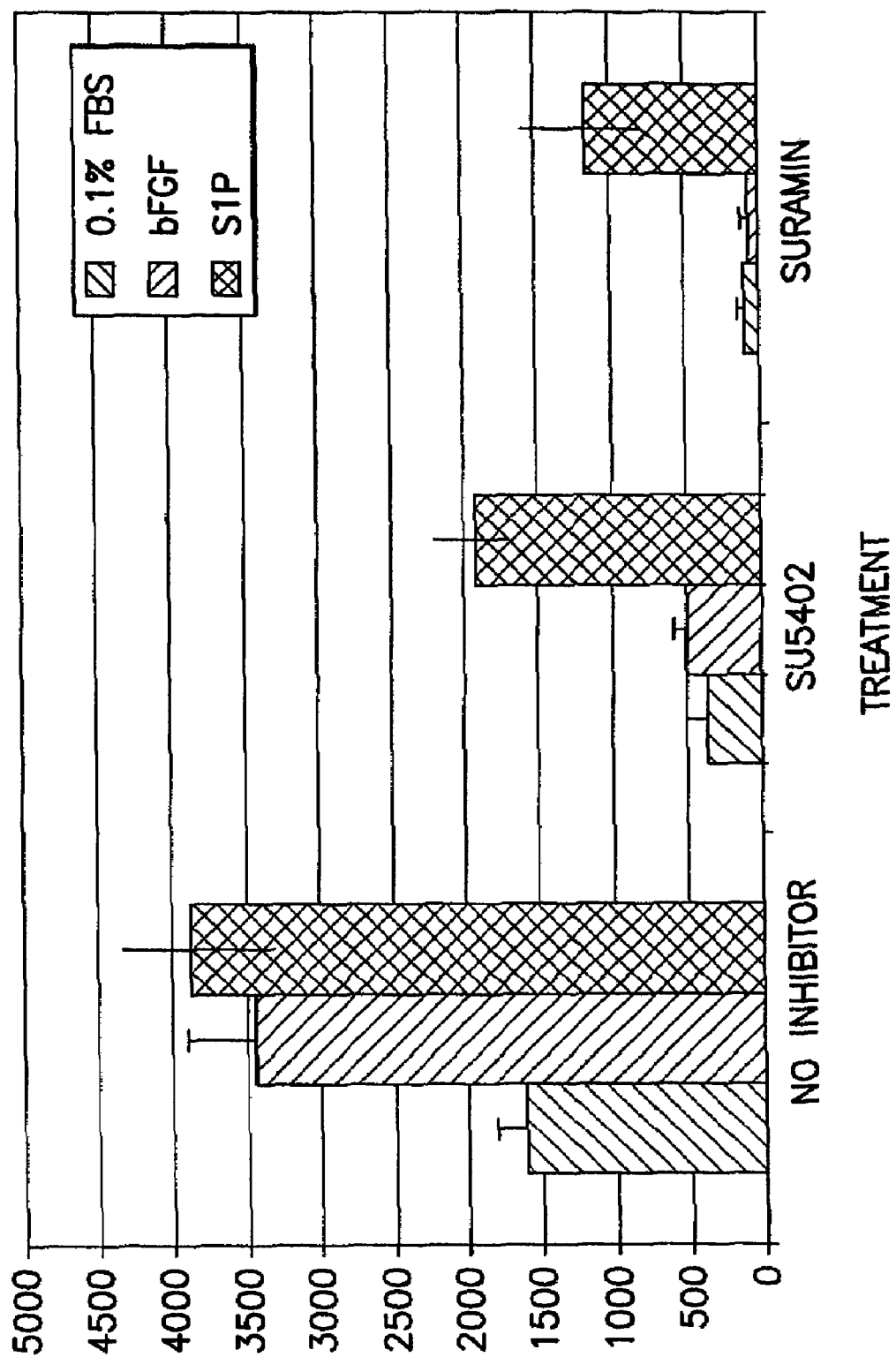

MODIFIED RECONSTITUTED BASEMENT MEMBRANE COMPOSITION FOR ASSAY SYSTEM

CROSS-REFERENCE TO RELATED APPLICATIONS

The present application is a continuation-in-part of U.S. application Ser. No. 10/909,636, filed Aug. 2, 2004 now abandoned, which claims the benefit of U.S. Provisional Patent Application No. 60/496,413, filed Aug. 20, 2003, the contents all of which are incorporated herein by reference.

FIELD OF THE INVENTION

The present invention relates generally to an extracellular matrix composition and cell culturing system to allow assessment of the effects of potential stimulators or inhibitors on various cell cultures.

BACKGROUND OF THE INVENTION

The harvest of cells from tissue for maintenance and propagation in vitro by tissue culture is a major tool in medical and biochemical research. Tissue culture is the technique or process of proliferating and/or supporting the metabolism of tissues or cells derived from organisms (plant or animal) in a formulated nutritive environment. Once isolated by gentle tissue dissociation, cells are incubated in nutritive media capable of supporting life functions. With few exceptions, cells require attachment to a substratum in order to perform normal metabolic functions, grow and divide. In tissue, the substratum, which provides the support for cell growth, is either the basement membrane or interstitial matrix. Basement membranes act not only as physical scaffolds and molecular filters, but also as solid-phase regulators of a variety of cellular processes, including attachment, motility and differentiation. Basement membranes can also modulate cellular growth by acting as a reservoir for growth factors and by prolonging their in vivo half-life.

The basement membrane is a specific type of extracellular matrix and is composed primarily of laminin and type IV collagen. The four major matrix components characteristic of basement matrices include laminin, collagen IV, entactin, nidogen and heparan sulfate proteoglycans (HSPG). The basement membrane also contains a number of growth factors, such as EGF, IGF-1, PDGF, TGF-beta, VEGF, and bFGF. Examples of commercially available basement membrane-derived extracellular matrices include, for example, ECM gel by Sigma-Aldrich, or Matrigel® by Becton, Dickinson & Company, which is extracted from the Engelbreth-Holm-Swarm (EHS) mouse tumor. This mouse tumor is rich in basement membrane proteins. At room temperature, Matrigel® Matrix gels to form reconstituted basement membrane and is similar in its structure, composition, physical property and ability to retain functional characteristics typical of basement membranes in vivo.

Matrigel® matrix supports differentiation of many cell types, including endothelial cells, epithelial cells, neurons and hepatocytes. When endothelial cells are plated on Matrigel®, the cells stop proliferating, display high motility and cell-cell communication. Furthermore, the cells align and form a three-dimensional network of tube or duct-like structures. The formation of these structures has been used as a model of endothelial cell differentiation, as well as the final step of the angiogenic cascade.

The use of Matrigel® in endothelial cell tube formation assays is one of the major in vitro applications of Matrigel® matrix. In these assays, the extent of endothelial cell tube length is measured and used as an indicator of endothelial cell tube formation. On typical extracellular matrix cell differentiation, cell tube formation can occur even in the absence of exogenously added growth factors due to the presence of growth factors in the matrix. This has limited the application of the extracellular matrix to studies involving inhibitory effects. In particular, it has been difficult to study stimulatory effects because the background tube formation is too high. As a result, tube formation assays have thus far not been sensitive enough for stimulation studies.

It is thus, one object of the present invention to provide a modified reconstituted basement membrane-derived extracellular matrix composition to reduce background cell tube formation, in the absence of added growth factors, by altering the matrix structure and/or by sequestering or blocking accessibility of the growth factors in the composition to cells.

Another object of the present invention is to provide a cell culturing system that allows direct assessment of potential angiogenesis stimulators, as well as inhibitors for their effects on cell tube formation of endothelial cells, and other cell types. It would also be beneficial to provide an assay system for studying action pathways of these stimulatory and inhibitory agents.

Additionally, an object of the present invention is to provide an assay system which is rapid and cost-effective, and which significantly increases the signal dynamic range.

SUMMARY OF THE INVENTION

The present invention relates to a modified reconstituted extracellular matrix composition and cell culturing system to allow assessment of potential effects of stimulators and/or inhibitors on various cell cultures. In some embodiments, the extracellular matrix composition is a modified reconstituted basement membrane composition. The inventive composition includes an extracellular matrix; and at least one exogenous component selected from: heparin, fibronectin and laminin. The pH of the composition can be adjusted to a basic pH. The extracellular matrix compositions provided herein are useful for coating a surface, such as a surface of a cell culture substrate. The coated substrates can be employed in, for example, endothelial cell tube formation assay systems.

In some embodiments, the present invention provides an extracellular matrix composition including an extracellular matrix; and exogenous fibronectin and heparin, the composition having a basic pH, wherein the extracellular matrix has a concentration of about 10 mg/ml, the exogenous fibronectin is present in concentrations of about 5 µg/ml to about 20 µg/ml and exogenous heparin is present in concentrations of about 200 µg/ml to about 800 µg/ml.

Moreover, in some embodiments, the present invention provides an extracellular matrix composition including an extracellular matrix; and exogenous laminin, the composition having a basic pH, wherein the extracellular matrix has a concentration of about 10 mg/ml and the exogenous laminin is present in concentrations of about 1 mg/ml to about 10 mg/ml.

Another aspect of the present invention is directed to a cell culturing system, which employs the inventive compositions provided herein as coating compositions for a substrate. The system includes a substrate; and a coating thereon of a coating composition including an extracellular matrix; and at least one exogenous component selected from heparin, fibronectin and laminin. The substrate may be a cell-culture substrate formed of any number of polymeric materials, glass, metal and microporous filters, for example.

Furthermore, the present invention provides a method of preparing the inventive compositions. The method includes: providing an extracellular matrix; and combining the provided extracellular matrix with at least one exogenous component selected from heparin, fibronectin and laminin. The method may further include adjusting the pH of the composition to a basic pH and/or adding sodium chloride to the composition.

Another aspect of the present invention is directed to a method for preparing the inventive cell culturing system. This method includes providing an extracellular matrix composition including an extracellular matrix and at least one exogenous component selected from heparin, fibronectin and laminin; and applying the composition to a substrate. The method further includes incubating the applied composition to allow polymerization thereof.

The compositions and systems of the present invention allow for evaluation of the ability of potential stimulators, as well as inhibitors to affect cell tube formation. Moreover, the inventive compositions significantly increase the signal dynamic range in cell tube formation assay systems.

BRIEF DESCRIPTION OF THE DRAWINGS

FIG. 5 is a graph showing the effect of inhibitors, SU5402 and Suramin, on HUVEC tube formation induced by stimulators, bFGF and S1P, on a modified extracellular matrix of the present invention.

DETAILED DESCRIPTION OF THE INVENTION

Figure 1:
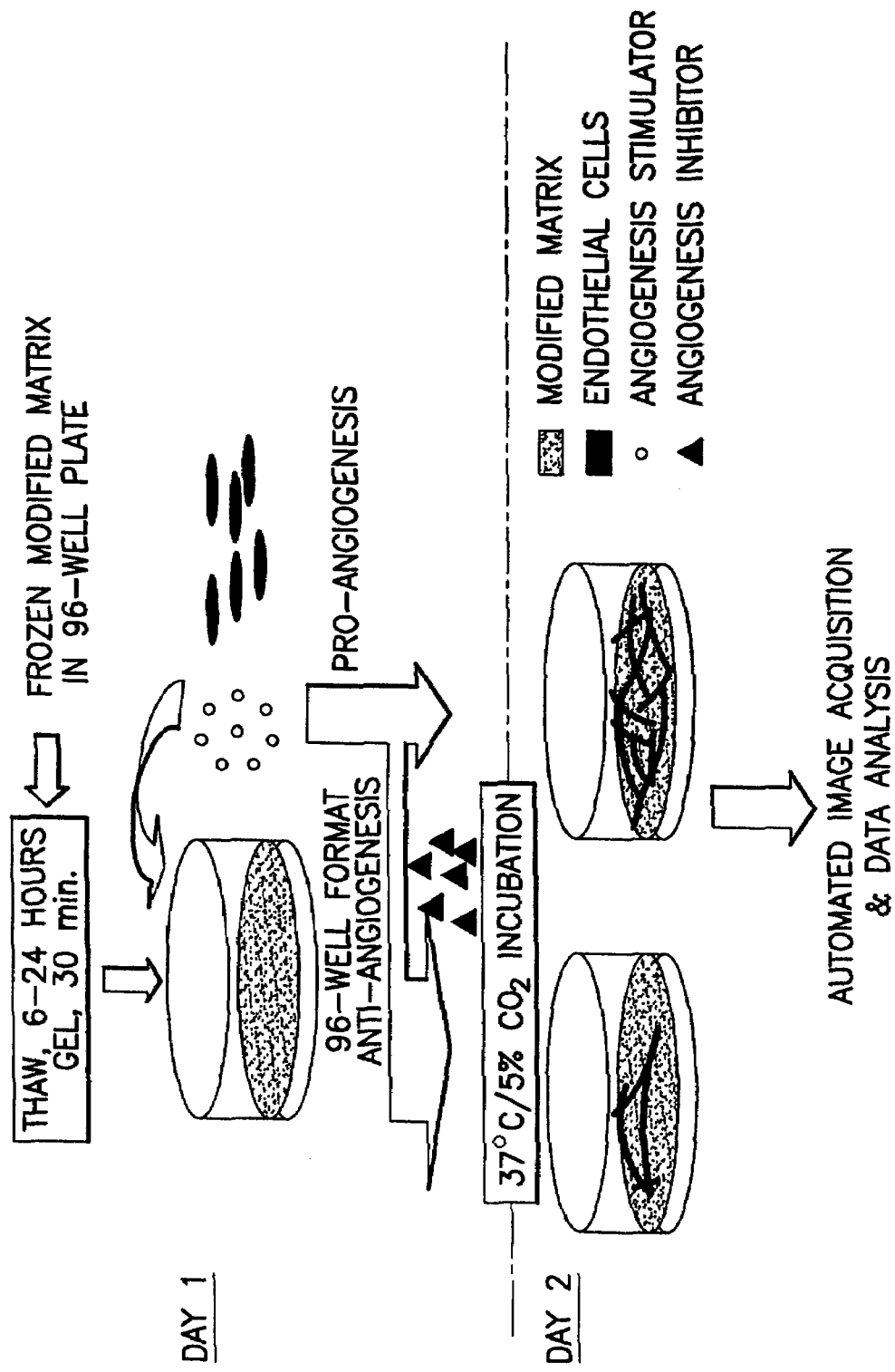
FIG. 1 is a schematic representation of an endothelial cell formation assay in a 96-well format, wherein the wells are coated with an extracellular matrix composition of the present invention (modified matrix).

A rapid and versatile endothelial cell tube formation assay system is highly desirable in angiogenesis research and drug discovery. Current assay systems are effective for studying angiogenesis inhibitors, but are not effective for the study of stimulators. The present invention is directed to a modified reconstituted extracellular matrix composition, which when used in an assay system is effective for studying both angiogenesis activation and inhibition. When employed in a cell based assay system, the inventive compositions were discovered to significantly increase the signal dynamic range, and enhance direct assessment of endothelial cell capillary-like structure formations. The present invention provides a medium for direct assessment of cell tube formation stimulators and inhibitors on various coated substrates.

In some embodiments, the present invention is directed to a modified reconstituted basement membrane, which includes components that alter the structure of the solidified gel and/or alter the accessibility of growth factors within the composition to cells such that cell tube formation (cell differentiation) is minimal in the absence of exogenous stimulators.

The present invention provides an extracellular matrix composition, which includes an extracellular matrix and at least one exogenous component selected from heparin, fibronectin and laminin. In one embodiment, the extracellular matrix is a basement membrane protein extract.

In some embodiments, the inventive composition has a basic pH. The pH of the composition is preferably between about 7.8 to about 8.5, more preferably about 8.0. The pH may be maintained with a Tris (hydroxymethyl) amino methane buffer. However, it is well within the contemplation of the present invention that any buffering component capable of maintaining the composition within the pH range of about 7.8 to 8.5 is suitable. Potential buffer systems for pH 8.0 include, but are not limited to, diethanolamine, triethanolamine, (1,3-bis(tris[Hydroxymethyl]methylamino)propane); 3-[N,N-bis(2-Hydroxyethyl)amino]-2-hydroxypropanesulfonic acid: DIPSO; (N-[2-Hydroxyethyl]piperazine-N'-[-4-butanesulfonic acid] HEPBS); (N-(4-(2-hydroxyethyl-1-piperazineethanesulfonic acid: HEPES); 3-(N-Morpholino)butane sulfonic acid: MOBS); (Piperazine-N,N'-bis[2-hydroxypropanesulfonic acid: POPSO); (N-tris(Hydroxymethyl)methyl-3-aminopropanesulfonic acid: TAPS; 3-(N-tris[Hydroxymethyl]methylamino)-2-hydroxypropanesulfonic acid: TAPSO); (N-tris(Hydroxyrnethyl)methyl-2-aminoethanesulfonic acid: TES; (N-tris(Hydroxymethyl)methylglycine: Tricine; N-ethylmorpholine, dimethylleucylglycine, sodium 5:5-diethyl barbituate and 2 amino, 2 methyl-1:3 propanediol.

In some embodiments, the inventive composition can include a Tris buffer at concentrations sufficient to buffer in the basic pH range. When present, the Tris buffer is preferably present at a concentration of about 0.01 M to about 0.05 M of the total composition. Tris base is commercially available from Fisher Scientific Co. (Hanover, Ill.) and Sigma-Aldrich (St. Louis, Mo.), for example.

Moreover, in some embodiments, the inventive composition includes a salt, such as sodium chloride. The sodium chloride, when present, is preferably at a concentration of about 0.03 M to about 0.15 M. While not wishing to be bound by any one theory, it is believed that pH and salt concentration can affect the density and strength of the polymerized basement membrane gel.

In one embodiment, the inventive composition includes an extracellular matrix, exogenous heparin and exogenous fibronectin, the composition having a basic pH. This composition may further include sodium chloride.

In a further embodiment, the composition includes an extracellular matrix and exogenous laminin, the composition having a basic pH. This composition may further include sodium chloride.

As defined herein, the "extracellular matrix" (of which the basement membrane is a specific type), is any material produced by cells and secreted into the surrounding medium. It is noted that the term "extracellular matrix" may be used interchangeably herein with the term "basement membrane". The extracellular matrix can be secreted by cells to form an interstitial basement membrane that forms the framework to which cells are attached. The basement membrane separates cells from mesenchymal connective tissue and provides spatial orientation and the stability required for the growth and differentiation of cells. Extracellular matrix molecules or basement membranes have also been implicated in the sequestration, storage and presentation of growth factors to tissues.

The basement membrane includes various components. However, its major component is laminin, followed by collagen IV, heparan sulfate proteoglycans, entactin and nidogen. These components polymerize in constant proportions when redissolved and allowed to reconstitute.

Extracellular matrix molecules or basement membranes are known in the art and are commercially available. For example, an extracellular matrix from EHS mouse sarcoma tumor is available as Matrigel® (Becton Dickinson Corp., Medford, Mass.), ECM gel (Sigma-Aldrich Co., St. Louis, Mo.), and Cultrex™ (Trevigen, Gaithersburg, Md.).

The term "extracellular matrix" is art recognized. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. Other extracellular matrix molecules are described in Kleinman et al., *J. Biometer. Sci. Polymer Edn.*, 5: 1-11, (1993), herein incorporated by reference. It is intended that the term "extracellular matrix" encompass a presently unknown extracellular matrix that may be discovered in the future, since its characterization as an extracellular matrix will be readily determinable by persons skilled in the art.

As described above, the compositions of the present invention include an extracellular matrix component. In one desired embodiment, the extracellular matrix is provided as a basement membrane protein extract, such as that disclosed in U.S. Pat. No. 4,829,000, the entire contents of which are hereby incorporated by reference. The protein extract is capable of polymerizing into a rigid stable gel (i.e., a 3-dimensional matrix) on heating. In particular, when incubated at temperatures from about 15-40° C. (preferably from about 22-37° C.) for a sufficient time, the extracellular matrix proteins polymerize. The proteins can remain in soluble form by maintaining a temperature of the composition lower than this range. Moreover, sodium chloride, or other salts, can be added to the composition to keep the proteins in soluble form and/or to affect the density and strength of the polymerized basement membrane gel. Preferably, the extracellular matrix component is maintained at a concentration of about 10 mg/ml of the total composition.

In some embodiments, the composition includes fibronectin, which is exogenously added to the extracellular matrix component. Preferably, the exogenous fibronectin is human fibronectin. The exogenous fibronectin is present at concentrations of about 5 μg/ml to about 20 μg/ml of the total composition, preferably at concentrations of about 8 μg/ml to 12 μg/ml of the total composition. It is known that fibronectin binds to collagen IV, and possibly other components of the extracellular matrix. Therefore, while not wishing to be bound by any one theory, it is likely that fibronectin is introduced into the matrix, thereby altering its structure. Human fibronectin is commercially available from Sigma-Aldrich (St. Louis, Mo.), for example.

Moreover, in some embodiments, exogenous heparin is present in the inventive compositions. The exogenous heparin is maintained at a concentration of about 200 μg/ml to about 800 μg/ml of the total composition, preferably at a concentration of about 300 μg/ml to about 600 μg/ml of the total composition. Heparin is known to bind to various growth factors, like VEGF and bFGF. Moreover, heparin is known to bind to collagen IV and to laminin. Therefore, while not wishing to be bound by any one theory, it is likely that heparin acts both by perturbing the structure of the extracellular matrix and by sequestering or blocking accessibility of growth factors in the composition to cells. Commercial sources of heparin include Calbiochem (La Jolla, Calif.) and Sigma-Aldrich (St. Louis, Mo.).

Furthermore, in some embodiments, the compositions of the present invention include exogenous laminin. The exogenous laminin is present at a concentration of about 1 mg/ml to about 10 mg/ml of the total composition, preferably at a concentration of about 2 mg/ml to about 4 mg/ml of the total composition. Laminin is known to bind to collagen IV. Moreover, laminin is known to contain binding sites for heparin. Therefore, while not wishing to be bound by any one theory, it is likely that laminin perturbs the structure of the extracellular matrix component. In desired embodiments, the laminin is human laminin. Human laminin is available from Sigma-Aldrich (St. Louis, Mo.), for example.

In addition to the components described above, the compositions of the present invention can also include various other components, which can affect the accessibility of the growth factors in the matrix to cells and/or which affect the structure of the matrix. These components include, but are not limited to, salts, diluents, heparan sulfate proteoglycans and/or neutralization antibodies. Additionally, suitable components of the composition can include those known in the art which do one or more of the following: affect the network density and strength when the proteins in the composition polymerize at temperatures of about 22° C. to about 37° C., sequester or block accessibility of growth factors in the matrix to cells, alter the crosslink states of the polymerized matrix, or assist in cell adhesion.

The diluents can include any cell culture medium which provides a condition that is compatible to cell culture. Diluents appropriate for growth and differentiation of epithelial cells can include, but are not limited to Dulbecco's Modified Eagle Medium (DMEM), MEM, M-199 and RPMI. Supplements, as are known in the art, may be added to the culture medium and include serum (e.g., FBS or calf serum), serum-containing supplements (NU-SERUM), and serum-free supplements (MITO+). A preferred cell culture medium for intestinal epithelial cells is DMEM supplemented with MITO+ Serum Extender (Collaborative Biomedical Products, Bedford, Mass.) to provide a fully defined, serum-free cell culture environment. Moreover, many classical media have been used to culture epithelial hepatocytes. Some examples of these are: Liebovitz L-15, DMEM/F-12, RPMI 1640, Waymouth's MB 752/1 and Williams Medium E. Hepatocytes can also be cultured in a serum-free medium named Hepatocyte Medium, available from Sigma-Aldrich (St. Louis, Mo.).

Diluents appropriate for growing endothelial cells include, but are not limited to, DMEM, HUVEC medium and EGM2-MV medium. For example, Human Umbilical Vein Endothelial Cells (HUVEC) can be cultured in HUVEC medium (Sigma-Aldrich, St. Louis, Mo.). Moreover, human umbilical cord endothelial cells (Cascade Biologics, Inc., Portland, Oreg.) can be cultured in EGM2-MV medium (Clonetics Corp., San Diego, Calif., a division of Biowhittaker).

The neutralization antibodies which are suitable include those compounds which affect the growth factor inherent in the extracellular matrix by titrating out the growth factor or blocking their effectiveness. Suitable neutralization antibodies may include, but are not limited to, antibodies against one of the following: TGF-beta, EGF, VEGF, PDGF, bFGF and IGF-1.

A wide variety of other materials, including bioactive proteins, may be copolymerized with the extracellular matrix composition of the present invention. These include, but are not limited to, cells, antibodies, enzymes, receptors, growth factors, additional components of the extracellular matrix, cytokines, hormones and drugs. Polymerization of the extracellular matrix proteins can bind such materials. Moreover, the extracellular matrix proteins can copolymerize with the materials. These biologically active materials, if present, can be readily available to the cultured cells to moderate or regulate their properties or behavior.

The present invention provides a method of preparing an extracellular matrix composition, such as a reconstituted basement membrane composition. The inventive compositions are useful for coating a surface, such as a surface of a cell culture substrate. The method of preparation includes providing an extracellular matrix; and combining the provided extracellular matrix with at least one exogenous component selected from heparin, fibronectin and laminin. The method may further include adjusting the pH of the composition to a basic pH. Moreover, the method may included the step of adding a salt, such as sodium chloride, to the composition. As described above, it is believed that pH and salt concentration can affect the density and strength of the polymerized basement membrane gel.

The method of preparing the inventive compositions is generally performed as follows. Initially, a frozen basement membrane protein extract, such as Growth Factor Reduced Matrigel® (Becton Dickinson Corp., Medford, Mass.) is thawed on ice. Once the basement composition is thawed, at least one exogenous component selected from fibronectin, heparin and lamin is added. The pH of the composition can be adjusted to a basic pH. The basement membrane is desirably maintained at a concentration of about 10 mg/ml of the final product. In some embodiments, after the basement membrane composition is thawed, fibronectin and heparin are added. In other embodiments, after the basement membrane composition is thawed, laminin is added. The composition is maintained at a temperature of about 4° C. for coating.

As described above, in some embodiments, the composition includes an extracellular matrix component, exogenous fibronectin and exogenous heparin. The composition may have a basic pH. In some embodiments, once the extracellular matrix component (e.g., a basement membrane protein extract) is thawed, fibronectin is added. The composition containing the exogenous fibronectin can then be dialyzed against a suitable cold dialysis buffer to adjust to a basic pH. For example, the composition can be dialyzed against the following dialysis buffer: DMEM (without $NaHCO_3$) containing an additional 40 mM NaCl/10 mM Tris plus 50 µg/ml gentamycin, adjusted to pH 8.0. In particular, the composition containing the fibronectin may be placed in a dialysis bag and dialyzed aseptically for about 18-20 hours. The contents are then removed and heparin is added. It is noted that, alternatively, heparin can be added prior to dialysis. The concentration of the extracellular matrix component in the final product is desirably about 10 mg/ml, that of exogenous fibronectin is desirably about 5 µg/ml to about 20 µg/ml, and that of exogenous heparin is desirably about 200 µg/ml to about 800 µg/ml. The composition is maintained at a temperature of about 4° C. for coating.

In other embodiments, the inventive composition includes an extracellular matrix component and exogenous laminin. The composition may have a basic pH. Once the extracellular matrix component is thawed as described above, laminin is added. The laminin may be added before or after the dialysis step. For example, in some embodiments, an extracellular matrix component, such as Growth Factor Reduced Matrigel® (Becton Dickinson Corp., Medford, Mass.), is first dialyzed against the following dialysis buffer: DMEM (without $NaHCO_3$) containing an additional 40 mM NaCl/10 mM Tris plus 50 µg/ml gentamycin, adjusted to pH 8.0. After 18-20 hours of aseptic dialysis, laminin may then be added, such that the concentration of the exogenous laminin in the final product is about 1 mg/ml to about 10 mg/ml. The composition is maintained at a temperature of about 4° C. for coating.

The present invention further provides a cell culturing system including: a substrate; and a coating thereon of a coating composition. The coating composition includes an extracellular matrix; and at least one exogenous component selected from heparin, fibronectin and laminin. In some embodiments, the extracellular matrix component to which the exogenous components are added is a basement membrane component, such that the coating composition is a modified reconstituted basement membrane composition. The coating composition may have a basic pH, Preferably, the pH is about 8.0.

Substrates for conventional cell culture research include plastic, glass, and micro porous filters (e.g., cellulosic, nylon, glass fiber, polyester, and polycarbonate). Substrates for bioreactors used in batch or continuous cell culture or in genetic engineering include hollow fiber tubes or micro carrier beads. Substrates for vascular or bone grafts include materials such as polytetrafluoroethylene (Teflon®), ceramics and related polymeric materials.

In some embodiments, the substrate is selected from the following: cellulose membranes, porous polycarbonate, porous polytetrafluoroethylene, nylon membranes, glass filters, porous polyethyleneterephthalate, polymethylpentane, polypropylene, polyethylene and combinations thereof.

Preferred substrate configurations contemplated by the present invention include multiwell plates (such as 24-well and 96-well plates), dishes (such as petri dishes), culture flasks, etc.

The present invention provides a method of preparing a cell-culturing system. The method includes providing an extracellular matrix composition including an extracellular matrix; and at least one exogenous component selected from heparin, fibronectin and laminin; and applying the composition to a substrate. The method also includes incubating the applied composition to allow polymerization thereof. A suitable substrate for coating may be selected from those described above, for example. The composition applied to the substrate may have a basic pH, which is desirably about 7.8 to about 8.5. For example, in some embodiments, the coating composition includes a Tris buffer at a concentration sufficient to buffer in the basic pH range. Moreover, in some embodiments, the applied composition may include sodium chloride, desirably at a concentration of about 0.03 M to about 0.15 M.

The coating procedure is generally performed as follows. Approximately 0.5 to 2.0 ml of the coating composition (desirably at about 4° C.) is applied to a well in a 6-well multiwell plate; about 0.25 to 1.0 ml is applied to a well in a 24-well multiwell plate; and about 50 µl to 100 µl is applied to a well in a 96-well plate. Furthermore, about 0.5 to 2.0 ml is applied to a 35 mm dish, 0.5 to 4.0 ml is applied to a 60 mm dish and 2.0 to 12.0 ml is applied to 100 mm dish. If desired, coated substrates can be frozen and stored at −20° C. before use, and then thawed prior to polymerizing the components of the coating composition. In embodiments where the substrate configuration is that of a multiwell plate, a mat cover may be used to seal each plate before putting on the lid to prevent the surface from over drying. Commercially available mat covers include, for example, to those supplied by SUN-SRI, Wilmington, N.C.

After application, the inventive composition is incubated to permit adsorption of the cell adhesion substance(s) in the composition to the substrate surface and to permit polymerization of the proteins in the composition. In particular, coated substrates are desirably incubated at temperatures from about 22° C. to about 37° C., and for a period of time of about 30 minutes to about 4 hours to effect polymerization of the components of the composition. If desired, the coating solution may be allowed to evaporate by drying at a temperature in this range and desirably at a relative humidity of 40-60%, and then rehydrated with cell culture medium or another sterile medium (e.g., sterile water) for about 2 hours at room temperature. The rehydration solution can then be removed just prior to assay setup. The final coated substrate is useful for assessing potential effects of stimulators, as well as inhibitors in that it produces a low background of cell tube formation or cell differentiation.

The compositions and cell culturing systems of the present invention can be used in various applications, including those known in the art for extracellular matrix and assay systems. These include in vitro, as well as in vivo applications. For example, one of the major in vitro applications includes the use of the inventive compositions in endothelial cell tube formation assays in response to exogenously added stimulators and/or inhibitors. Endothelial cell tube formation has been used as a model of endothelial cell differentiation, as well as the final step of the angiogenic cascade. Previously, background cell tube formation was too high in assays employing prior extracellular matrix compositions. This limited the application of the prior compositions to studies involving potential inhibitors of cell differentiation and/or angiogenesis. In contrast, the extracellular matrix compositions of the present invention are useful for stimulation studies, as well as inhibition studies. For example, with the present compositions, in the absence of an exogenous stimulator, background cell tube formation is insignificant. Thus, endothelial cell tube formation, and tube formation with other cell types, can be monitored in response to exogenously added stimulators, such as bFGF and sphinosine-1-phosphate. Additionally, cell differentiation of mammary ephelial cell acini formation, or neurite outgrowth can be studied using the inventive compositions. With respect to in vivo uses, the compositions of the present invention can be mixed with angiogenesis stimulators, inhibitors and/or tumor cells in a plug assay, which can be used to induce (e.g., with stimulators) or suppress (e.g., with inhibitors) blood vessel growth in vivo.

The assay system of the present invention can be used to test various inhibitors or stimulators to determine their effectiveness in a cell study. Stimulators can include growth factors which are known in the art. For example, these can include one or more of platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-β1, TGF β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor. Additional growth factors are described in Sporn and Roberts, *Peptide Growth Factors and Their Receptors I*, Springer-Verlag, New York (1990), which is hereby incorporated by reference. The term "growth factors" is intended to encompass presently unknown growth factors that may be discovered in the future, since their characterization as a growth factor will be readily determinable by persons skilled in the art.

Many growth factors are available commercially from vendors, such as Sigma Chemical Co., St. Louis, Mo.; Collaborative Research, Los Altos, Calif.; Genzyme, Cambridge, Mass.; Boehringer, Germany; R&D Systems, Minneapolis, Minn.; Genetech, San Francisco, Calif.; and GIBCO, Grand Island, N.Y. The commercially available growth factors may be obtained in both natural and recombinant forms.

The following examples are for illustrative purposes and are not intended to, in any way, limit the embodiments and uses of the present invention.

EXAMPLES

Example 1

Preparation of a Modified Extracellular Matrix Composition

A modified reconstituted basement membrane composition of the present invention was prepared as follows. Frozen Growth Factor Reduced Matrigel® (Becton Dickinson Corp., Medford, Mass.) was thawed on ice. After thawing, human fibronectin was added such that the concentration in the final product was about 8 µg/ml to about 12 µg/ml. The composition containing the exogenous fibronectin was dialyzed against the following dialysis buffer: DMEM (without NaHCO$_3$) containing an additional 40 mM NaCl/10 mM Tris plus 50 µg/ml gentamycin, adjusted to pH 8.0. In particular, the composition containing the fibronectin was placed in a dialysis bag and dialyzed aseptically for about 18-20 hours. The contents were then removed and heparin was added. The concentration of the extracellular matrix component in the final product was about 10 mg/ml, and that of the exogenous heparin was about 300 µg/ml to about 600 µg/ml. The composition was maintained at a temperature of about 4° C. prior to coating cell culture substrates.

Example 2

General Coating Procedure

Multiwell plates were prepared as follows. Approximately 50 µl of a solution (at 4° C.) of either the modified reconstituted basement membrane composition described in Example 1 or standard Growth Factor Reduced Matrigel® (Becton Dickinson Corp., Medford, Mass.) was added to wells of BD Falcon Black/clear 95-well micro plates. A mat cover was used to seal each plate before putting on the lid. The plates were frozen and stored at −20° C. before use.

Example 3

General Procedure for Endothelial Cell Tube Formation Assay

With reference to FIG. 1, angiogenesis stimulators can be evaluated for their ability to enhance HUVEC tube formation using the compositions and cell culturing systems of the present invention. In particular, FIG. 1 shows stimulators being evaluated on the coated surface of wells of a 96-well plate. The bottom surface of the wells are shown as coated with the modified matrix composition of the present invention. On day 1, a potential angiogenesis stimulator is added to the coated surface, along with endothelial cells in cell medium. As shown in FIG. 1, the compositions and cell culturing systems of the present invention can also be used in inhibitor studies. In inhibitor studies, the potential inhibitor is included in a well, in addition to at least one known stimulator and the endothelial cells in cell medium. After an appropriate incubation period, typically 24 hours at 37° C./5% CO2 (day 2), images of the wells are acquired, and tube length is quantified as a measure of cell tube formation.

Example 4

Stimulator Studies

Known stimulators were chosen to evaluate the performance of an inventive basement membrane composition vs. a prior basement membrane composition. The chosen stimulators were bFGF and spinosine-1-phosphate (S1P). Coated plates prepared as described above in Example 2 were thawed at about 4° C. for a period of about 4 to 5 hours. The components of the composition were then allowed to polymerize at 37° C., 5% $CO_2$ for approximately 30 minutes immediately before assay setup. For stimulator studies, HUVEC (P3-P5) were harvested at about 70% cell confluence. About 50 μl of cells at $4\times10^5$/ml in 0.1% FBS/EBM-2 medium supplemented with or without the angiogenesis stimulators were seeded onto 96-well plates containing the pre-solidified (i.e., polymerized) modified reconstituted basement membrane composition (inventive) or a standard Matrigel® matrix (BD Growth Factor Reduced Matrigel® Matrix). The assembled assays were allowed to incubate in a 37° C. incubator with 5% $CO_2$ for approximately 16 to 18 hours. Compounds were dissolved in DMF or water according to manufacturer's instructions.

At the end of each assay, assay medium was removed and plates were washed once with HBSS. 50 μl Calcein AM at 8 μg/ml in HBSS was added to each well and plates were incubated in a 37° C./5% $CO_2$ incubator for 35 minutes followed by washing once in HBSS. Images were acquired with a 2× objective lens on an automated Gen-1 Cell-based Screening System (Universal Imaging Corporation™). Total tube length of each well was measured using a revised (from previous) MetaMorph® Journal. Excel data was imported and analyzed using BD Gentest MPM/ADMET Software Program from BD Biosciences Discovery Labware.

Figure 2:
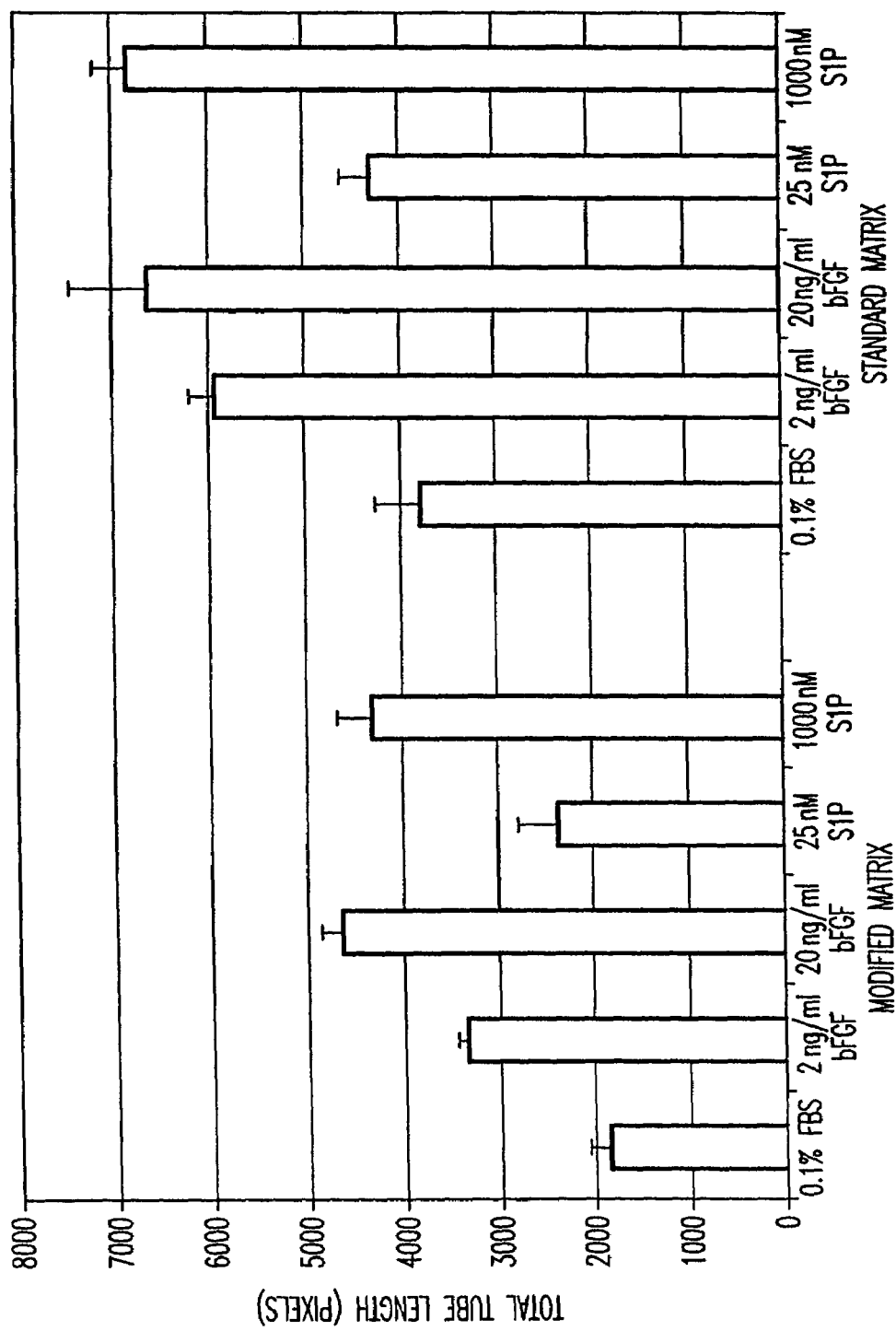
FIG. 2 is a graph showing the effect of different concentrations of stimulatory agents on cell tube formation on a modified extracellular matrix of the present invention versus a standard extracellular matrix.

As shown in FIG. 2, the tube length of HUVEC (a measure of cell tube formation) was compared using the different matrices in the presence of the stimulators, bFGF and S1P. The results show that the inventive composition (modified matrix) increases signal dynamic range over a standard basement membrane composition (standard matrix). The stimulators, bFGF and S1P, were incubated with HUVEC at the indicated concentrations on the matrices. Each bar represents the mean +/− standard Deviation (n=4). FIG. 2 shows that the signal dynamic range was increased overall using the modified matrix of the present invention verses the standard matrix.

Figure 3A:
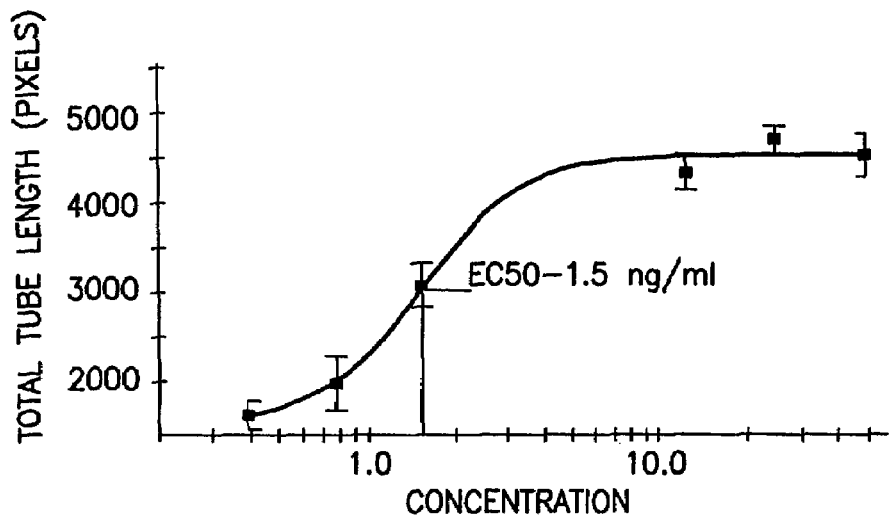
FIG. 3A is a graph showing the dose response of bFGF in inducing HUVEC tube formation on a modified extracellular matrix of the present invention.
Figure 3B:
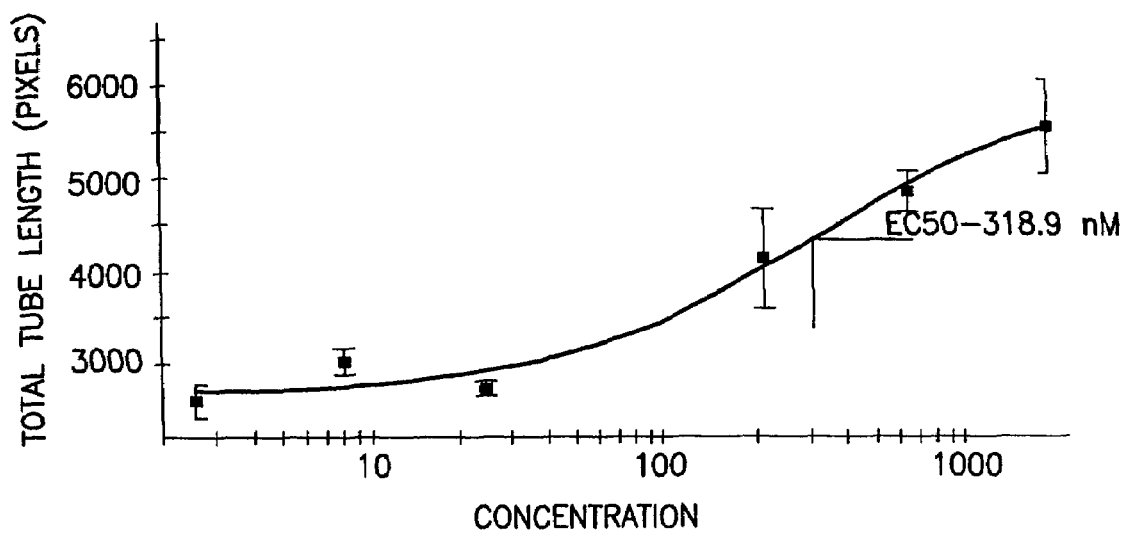
FIG. 3B is a graph showing the dose response of sphinosine-1-phosphate (S1P) in inducing HUVEC tube formation on a modified extracellular matrix of the present invention.

As shown in FIGS. 3A and 3B, the assay system allowed applicants to determine the $EC_{50}$ values of bFGF (FIG. 3A) and S1P (FIG. 3B) in inducing HUVEC tube formation. The dose response of the stimulators in inducing tube formation was obtained on the modified matrix (inventive) at the indicated concentrations. The stimulators, at indicted concentrations, were added to each well. Each data point represents the mean +/− Standard Deviation (n=4). The results show a dose-dependent stimulation of capillary-like structure formation by bFGF (FIG. 3A) and S1P (FIG. 3B). The inventive cell culturing system allowed applicants to determine an $EC_{50}$ value for bFGF of 1.5 ng/ml, and an $EC_{50}$ value for S1P of 318.9 nM.

Example 5

Inhibitor Studies

Figure 4:
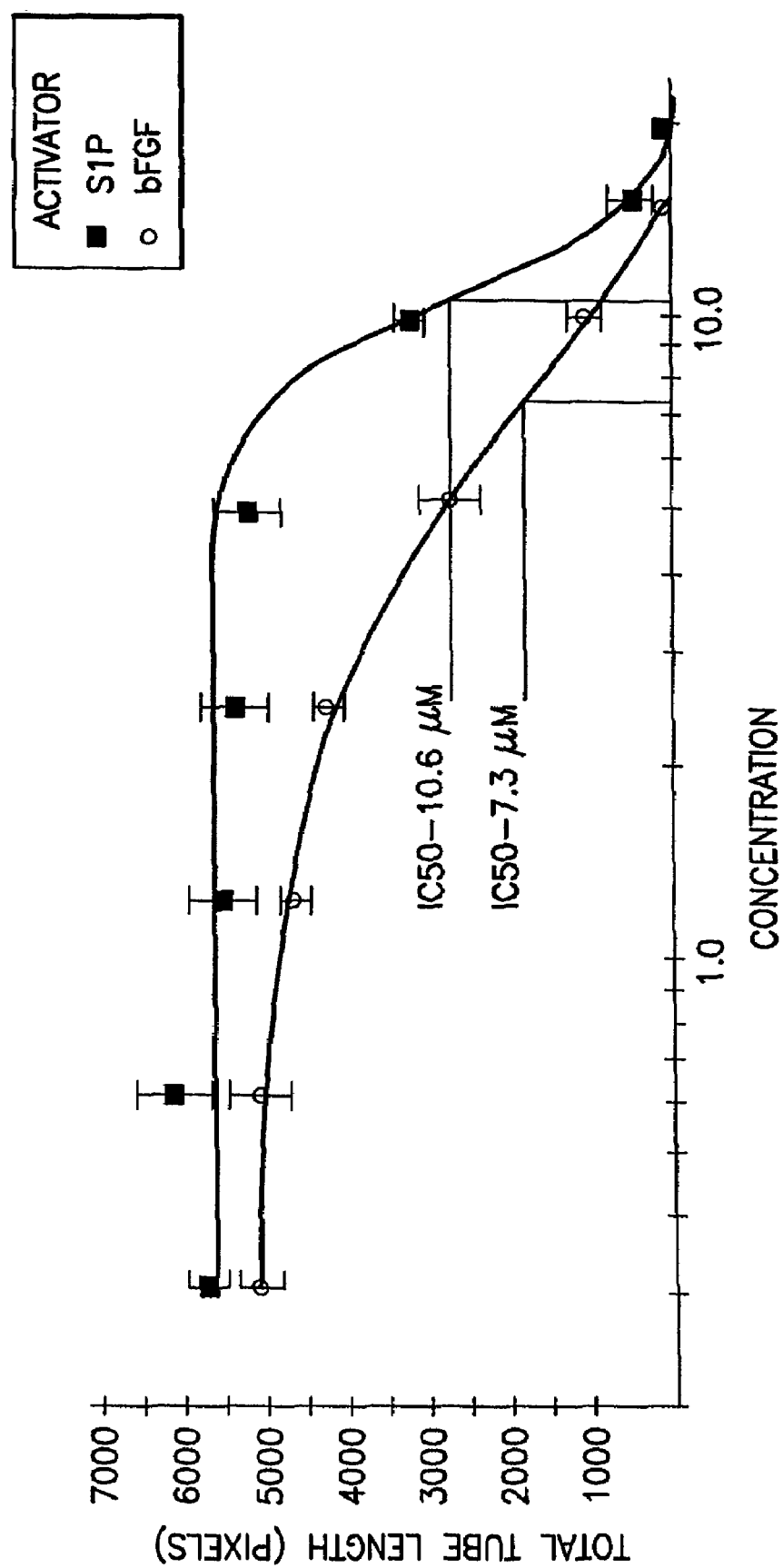
FIG. 4 is a graph showing the dose response of Suramin in HUVEC tube formation induced by stimulators, bFGF and S1P, on a modified extracellular matrix of the present invention.

Inhibitor studies were performed as generally described in Example 4, except that for these studies, an inhibitor was included in the assay, in addition to a known stimulator. Data was obtained on the modified matrix (inventive). As shown in FIG. 4, the total tube length induced by stimulators, bFGF or S1P, was measured in the presence of various concentrations of an inhibitor (Suramin). Stimulators, bFGF or S1P, were added to HUVECs at 20 ng/ml and 1 μM, respectively. Suramin of indicated concentrations was added to HUVEC in bFGF or S1P prior to adding the mixtures to each well. Each data point represents the mean +/− standard deviation (n=4). FIG. 4 shows that Suramin inhibited HUVEC tube formation induced by bFGF or S1P activation pathways with distinct $IC_{50}$ values. In particular, the $IC_{50}$ value of Suramin inhibition of tube formation stimulated by bFGF was 7.3 μM, and the $IC_{50}$ value of Suramin inhibition of tube formation stimulated by S1P was 10.6 μM.

With reference now to FIG. 5, the effects of inhibitors (SU5402 and Suramin) on HUVEC tube formation induced by stimulators (bFGF and S1P) is shown. Data was obtained on the modified matrix (inventive). Stimulators, bFGF or S1P, were added to HUVECs in EBM-2 containing 0.1% FBS at a final concentration of 20 ng/ml and 1 μM, respectively. Suramin at 15 μM (in medium) or SU5402 at 25 μM (in 0.1% DMF) were added to HUVECs in 0.1% FBS, or bFGF, or S1P, prior to adding the mixtures to the wells. As shown in FIG. 5, SU5402 (an FGFR1 tyrosine kinase inhibitor) partially inhibited S1P induced tube formation, raising the possibility that induction of bFGF could be one mechanism of S1P action. Moreover, SU5402 completely inhibited tube formation stimulated by bFGF. Furthermore, the graph shows that Suramin inhibited both S1P and bFGF induced tube formation. Each bar represents the mean +/− standard deviation (n=4).

Modified reconstituted basement membrane of the present invention increased dynamic range and allowed assessment of the effect of both stimulators and inhibitors. The assay system allowed one to determine $EC_{50}$ values of stimulators in inducing HUVEC tube formation and $IC_{50}$ values of inhibitors of tube formation stimulated by the stimulatory agents. This assay system offers an opportunity to study action pathways of angiogenesis modulators in endothelial cell tube formation.

It will be apparent that the present invention has been described herein with reference to certain preferred or exemplary embodiments. The preferred or exemplary embodiments described herein may be modified, changed, added to, or deviated from without departing from the intent, spirit and scope of the present invention, and it is intended that all such additions, modifications, amendments and/or deviations be included within the scope of the following claims.

What is claimed is:

1. A composition for coating a surface comprising:
   (a) a growth factor reduced extracellular matrix extracted from Engelbreth-Holm-Swarm mouse sarcoma tumor;
   (b) fibronectin which is exogenous to said growth factor reduced extracellular matrix; and
   (c) heparin which is exogenous to said growth factor reduced extracellular matrix; wherein endothelial cell tube formation in the composition is minimal in the absence of an exogenous stimulator.

2. The composition of claim 1, wherein the growth factor reduced extracellular matrix comprises laminin.

3. The composition of claim 1, wherein the composition has a basic pH.

4. The composition of claim 3, wherein the pH of the composition is between about 7.8 to about 8.5.

5. The composition of claim 1, further comprising a Tris buffer at a concentration sufficient to buffer in the basic pH range.

6. The composition of claim 5, wherein the Tris buffer is present at a concentration of about 0.01 M to about 0.05 M.

7. The composition of claim 1, further comprising sodium chloride.

8. The composition of claim 7, wherein the sodium chloride is present at a concentration of about 0.03 M to about 0.15 M.

9. The composition of claim 1, wherein the growth factor reduced extracellular matrix is present at a concentration of about 10 mg/mL of the composition.

10. The composition of claim 1, wherein the fibronectin which is exogenous to the growth factor reduced extracellular matrix is present at a concentration of about 5 µg/ml to about 20 µg/ml of the composition.

11. The composition of claim 1, wherein the heparin which is exogenous to said growth factor reduced extracellular matrix is present at a concentration of about 200 µg/ml to about 800 µg/ml of the composition.

12. The composition of claim 1, wherein endothelial cell tube formation in the composition is insignificant in the absence of an exogenous stimulator.

13. The composition of claim 1, wherein the growth factor reduced extracellular matrix is solubilized.

14. The composition of claim 1, wherein the growth factor reduced extracellular matrix is polymerized.

15. The composition of claim 14, wherein the composition is polymerized by incubating the composition at a temperature from about 22° C. to about 37° C. for a period of time of about 30 minutes to about 4 hours to allow polymerization thereof.

16. The composition of claim 14, wherein the growth factor reduced extracellular matrix is a reconstituted extracellular matrix.

17. The composition of claim 16, wherein the reconstituted extracellular matrix comprises the fibronectin which is exogenous to said growth factor reduced extracellular matrix and the is heparin which is exogenous to said growth factor reduced extracellular matrix therethroughout.

18. An extracellular matrix composition for coating a surface comprising:
   (a) a growth factor reduced extracellular matrix extracted from Engelbreth-Holm-Swarm mouse sarcoma tumor;
   (b) fibronectin which is exogenous to the growth factor reduced extracellular matrix; and
   (c) heparin which is exogenous to the growth factor reduced extracellular matrix;
   the extracellular matrix composition having a basic pH; and
   wherein the growth factor reduced extracellular matrix is present at a concentration of about 10 mg/mL of the composition, the fibronectin which is exogenous to the growth factor reduced extracellular matrix is present at a concentration of about 5 µg/mL to about 20 µg/mL of the composition, and the heparin which is exogenous to the growth factor reduced extracellular matrix is present at a concentration of about 200 µg/mL to about 800 µg/mL of the composition.

19. A cell culturing system comprising:
   a substrate; and
   a polymerized coating formed on the substrate from a coating composition comprising:
   (a) a growth factor reduced extracellular matrix extracted from Engelbreth-Holm-Swarm mouse sarcoma tumor;
   (b) fibronectin which is exogenous to said growth factor reduced extracellular matrix; and
   (c) heparin which is exogenous to said growth factor reduced extracellular matrix;
   wherein the polymerized coating is formed on the substrate by incubating the coating composition with the substrate at a temperature from about 22° C. to about 37° C. for about 30 minutes to about 4 hours;
   wherein said polymerized coating includes therethroughout said exogenous components; and
   wherein endothelial cell tube formation in the polymerized coating is minimal in the absence of an exogenous stimulator.

20. The system of claim 19, wherein the coating composition has a basic pH.

21. The system of claim 19, wherein the substrate is selected from the group consisting of cellulose membranes, porous polycarbonate, porous polytetrafluoroethylene, nylon membranes, glass filters, porous polyethyleneterephthalate, polymethylpentane, polypropylene, polyethylene and combinations thereof.

22. The system of claim 19, wherein endothelial cell tube formation in the polymerized coating is insignificant in the absence of an exogenous stimulator.

* * * * *